United States Patent [19]
Shishido et al.

[11] Patent Number: 5,618,831
[45] Date of Patent: Apr. 8, 1997

[54] COMPOSITION AND METHOD FOR TREATING CANCER

[75] Inventors: Tadao Shishido; Masayuki Kawakami; Akihiko Ikegawa; Toshinao Ukai, all of Kanagawa-ken, Japan; Keizo Koya; Lan B. Chen, both of Lexington, Mass.

[73] Assignees: Fuji Photo Film Co., Ltd., Kanagawa, Japan; Dana Farber Cancer Institute, Boston, Mass.

[21] Appl. No.: 242,834

[22] Filed: May 16, 1994

Related U.S. Application Data

[63] Continuation-in-part of Ser. No. 138,061, Oct. 19, 1993, Pat. No. 5,476,945.

[30]     Foreign Application Priority Data

Nov. 17, 1992  [JP]  Japan ..................... 4-305769

[51] Int. Cl.$^6$ ..................... A61K 31/425; A61K 31/505; A61K 31/44; A61K 31/47
[52] U.S. Cl. ................. 514/366; 514/367; 514/275; 514/267; 514/260; 514/297; 514/310; 514/313
[58] Field of Search ..................... 514/366, 367, 514/275, 267, 260, 297, 310, 313

*Primary Examiner*—Jerome D. Goldberg
*Attorney, Agent, or Firm*—Sughrue, Mion, Zinn, Macpeak & Seas

[57]         ABSTRACT

A pharmaceutical composition for treatment of cancer in an animal comprising:

(A) a therapeutically effective amount of at least one compound selected from the group consisting of compounds represented by the General Formula (I).

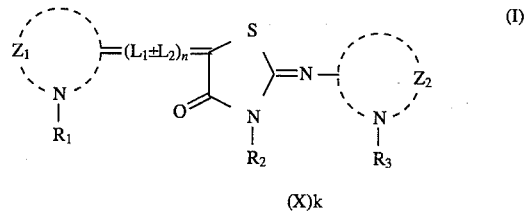

wherein $Z_1$ and $Z_2$, which may be the same or different, each represents an atomic group necessary to form a 5- or 6-membered ring;

$R_1$, $R_2$ and $R_3$, which may be the same or different, each represents an alkyl group or an aryl group;

$L_1$ and $L_2$ each represents a methine group or a substituted methine group;

X represents a pharmaceutically acceptable anion;

k represents a number necessary for electrical charge balance;

n represents 0 or 1; and (B) a pharmaceutically acceptable carrier or diluent.

9 Claims, No Drawings

COMPOSITION AND METHOD FOR TREATING CANCER

CROSS-REFERENCE TO RELATED APPLICATION

The present application is a continuation-in-part of U.S. application Ser. No. 08/138,061 filed Oct. 19, 1993, now Pat. No. 5,476,945.

FIELD OF THE INVENTION

This invention relates to a composition and a method useful in treating a number of different types of cancers, and, in particular, carcinomas or melanomas. More particularly, this invention relates to a pharmaceutical composition containing a select class of rhodacyanine dyes useful in treating cancers and to a method for treating cancers using this composition.

BACKGROUND OF THE INVENTION

Cancer is a serious health problem throughout the world. As a result, an extensive amount of research has been conducted to develop therapies appropriate to the treatment and alleviation of cancer in humans.

In the chemotherapeutic area, research has been conducted to develop anti-tumor agents effective against various types of cancer. Often anti-tumor agents developed and found effective against cancerous cells, unfortunately, are toxic to normal cells. This toxicity gives rise to hair loss, nausea, weight loss, vomiting, hallucination, fatigue, itching, loss of appetite, etc., when administered to a patient needing cancer therapy.

Further, conventionally used chemotherapeutic agents do not have the effectiveness desired or are not as broadly effective against different types of cancers as is desired. As a result, chemotherapeutic agents which have greater effectiveness against cancers and which have a higher degree of selectivity for killing cancer cells with no or minimal effect on normal healthy cells is desired. Highly effective and selective anti-tumor agents, in particular, against cancers of the colon, bladder, prostate, stomach, pancreas, breast, lung, liver, brain, testis, ovary, cervix, skin, vulva, small intestine and like organs is desired. Anti-tumor agents against cancers such as colon cancer and melanomas are also particularly desired because of the lack of any particularly effective therapy at present.

Certain types of cyanine dyes have been disclosed as having anti-cancer activity (see, for example, Japanese Kokai 79/151,133, 80/31,022, 80/69,513, 80/100,318, Japanese Koho 89/52,325, E.P. No. 286252A2). However, these cyanine dyes cannot be used effectively for therapy in humans because of their high toxicity to healthy cells as well as to cancer cells. In addition, these cyanine dyes often are poorly soluble in diluents acceptable for human administration.

Furthermore, a solution of drug having an absorption at short wavelength, i.e., the solution of light color is preferably acceptable in medical and pharmaceutical fields and the like since it does not cause patient a feeling of uneasiness rather than a solution of dark color does. In this connection, certain rhodacyanine dyes have high toxicity to cancer cells and low toxicity to normal cells, but the dyes are not satisfactory in terms of absorption at short wavelength, and as a result, it is desired to have a solution of drug having an absorption at shorter wavelength.

SUMMARY OF THE INVENTION

Accordingly, an object of this invention is to provide pharmaceutical compositions effective against cancer cells.

A further object of the present invention is to provide pharmaceutical compositions useful in the treatment of cancer where a higher degree of selectivity against cancer cells exists than has been found for prior art anti-tumor agents.

An even further object of the present invention is to provide pharmaceutical compositions effective in treatment against carcinomas and melanomas for which prior art treatments have not been found to be particularly effective.

A still further object of this invention is to provide pharmaceutical compositions and a method using the pharmaceutical compositions useful in the treatment and alleviation of cancer in mammals such as humans.

A still further object of this invention is to provide pharmaceutical compositions having an absorption at short wavelength.

These and other objects of the present invention will be apparent from the following description and Examples.

As a result of extensive research, it has now been found that the above-objects of the present invention are satisfied by classes of rhodacyanine dyes, heretofore known primarily for their use in the fabrication of photosensitive materials, which are effective in treating cancer and, in particular carcinomas and melanomas.

In one embodiment, the present invention provides a pharmaceutical composition containing (A) a therapeutically effective amount of a methine compound selected from the group consisting of compounds of the following Formula (I):

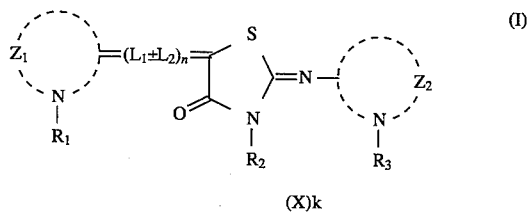

wherein $Z_1$ and $Z_2$, which may be the same or different, each represents, together with a nitrogen atom, an atomic group necessary to form a 5- or 6- membered ring;

$R_1$, $R_2$ and $R_3$, which may be the same or different, each represents an alkyl group or an aryl group;

$L_1$ and $L_2$ each represents a methine group or a substituted methine group;

X represents a pharmaceutically acceptable anion;

K represents a number necessary for electrical charge balance;

n represents 0 or 1; and (B) a pharmaceutically acceptable carrier or diluent.

In another embodiment, the present invention provides a method of treatment of cancer comprising administering the composition described above to a mammalian host in need of such treatment.

DESCRIPTION OF THE PREFERRED EMBODIMENTS

Preferred embodiments of this invention include compositions and method as described above where the methine compound is a compound selected from the group consisting of compounds of the following Formula (II) to (III) set forth below:

Formula (II):

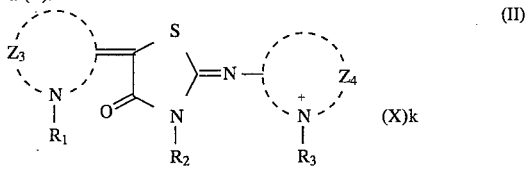

(II)

wherein $Z_3$ represents, together with a nitrogen atom, an atomic group necessary to form a thiazolidine ring, a thiazoline ring, a benzothiazoline ring, a tetrahydrobenzothiazoline ring, a naphthothiazoline ring, an oxazolidine ring, an oxazoline ring, a benzoxazoline ring, a tetrahydrobenzoxazoline ring, a naphthoxazoline ring, a dihydroquinoline ring, a dihydropyridine ring, a benzoselenazoline ring, an indolenine ring, an imidazoline ring, a benzimidazoline ring, a dihydroisoquinoline ring, or a dihydronaphthothiazoline ring;

$Z_4$ represents together with $N^+$, an atomic group necessary to form a pyridinium ring, a thiazolium ring, a pyrimidinium ring, a benzothiazolium ring, a quinolinium ring, a naphthothiazolium ring, an oxazolidinium ring, an oxazolium ring, a benzoxazolium ring, a naphthoxazolium ring, an isoquinolinium ring, a benzoselenazolium ring, or an indolenium ring;

$R_1$, $R_2$, and $R_3$, which may be the same or different, each represents an alkyl group having 1 to 10 carbon atoms or an aryl group having 1 to 10 carbon atoms; and X and k have the same meanings as defined above.

Formula (III):

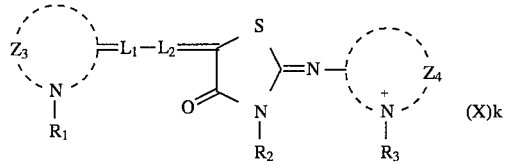

(III)

wherein $Z_3$, $Z_4$, $R_1$, $R_2$, $R_3$, k and X have the same meanings as defined for Formula (II).

In the specific embodiments of the present invention, the pharmaceutical compositions of the present invention comprise, as an anti-tumor agent, a compound selected from the group consisting of the compounds having the general formulae (I) to (III), together with a suitable pharmacologically acceptable carrier or a diluent.

In greater detail, in the General Formulas (I) to (III)

$Z_1$ and $Z_2$, which may be the same or different, each represents, together with a nitrogen atom, an atomic group necessary to form a saturated or unsaturated 5- or 6-membered ring which may contain two or more nitrogen atoms, one or more oxygen atoms, sulfur atoms or selenium atoms as hetero atoms and may further be condensed with another ring such as a saturated or unsaturated ring.

$R_1$, $R_2$, and $R_3$, which may be the same or different, each represents a substituted or unsubstituted alkyl group or aryl group.

X represents a pharmaceutically acceptable anion.

k is a number necessary for electrical charge balance and usually 0 or 1.

n is 0 or 1.

$Z_3$ represents, together with a nitrogen atom connected to $R_1$ group, an atomic group necessary to form a thiazolidine ring, a thiazoline ring, a benzothiazoline ring, a tetrahydrobenzothiazoline ring, a naphthothiazoline ring, an oxazolidine ring, an oxazoline ring, a benzoxazoline ring, a tetrahydrobenzoxazoline ring, a naphthoxazoline ring, a dihydroquinoline ring, a dihydropyridine ring, a benzoselenazoline ring, an indolenine ring, an imidazoline ring, a benzimidazoline ring, a dihydroisoquinoline ring, or a dihydronaphthothiazoline ring.

These heterocyclic rings may be substituted with one or more substituents or may be condensed with another ring such as a saturated or unsaturated ring, e.g., a cyclohexene ring, a benzene ring, a naphthalene ring, a thiophene ring, a furan ring, a pyrrole ring and the like. Suitable examples of substituents include hydrogen atoms, $C_1$–$C_{10}$ alkyl group (e.g., methyl, trifluoromethyl, ethyl, hydroxyethyl, propyl, isopropyl, butyl, iso-butyl, tert-butyl, benzyl, etc.), $C_1$–$C_{10}$ alkoxy groups (e.g., methoxy, methylenedioxy, ethoxy, propoxy, butoxy, benzyloxy, etc.), halogen atoms (e.g., chlorine, bromine, fluorine and iodine), $C_6$–$C_{10}$ aryl groups (e.g., phenyl, tolyl, etc.), $C_6$–$C_{10}$ aryloxy groups (e.g., phenoxy, 4-methylphenoxy, 4-chlorophenoxy, etc.), $C_2$–$C_{10}$ alkoxy carbonyl groups (e.g. methoxy carbonyl, ethoxy carbonyl, propoxy carbonyl, butoxy carbonyl, benzyloxy carbonyl, etc.), hydroxyl groups, mercapto groups, cyano groups, nitro groups, carboxyl groups, $C_1$–$C_{10}$ acyl groups (e.g., acetyl, propionyl, benzoyl, etc.), $C_2$–$C_{10}$ acetoxy groups (e.g., acetyloxy, propionyloxy, benzoyloxy, etc.), $C_2$–$C_{10}$ acylamino groups (e.g., acetylamino, propionylamino, benzoylamino, etc.), $C_1$–$C_{10}$ sulfonylamino groups (e.g., methanesulfonylamino, benzenesulfonylamino, etc.), $C_1$–$C_{10}$ carbamoyl groups (e.g., carbamoyl, methylcarbamoyl, acetylcarbamoyl, methanesulfonylcarbamoyl, phenylcarbamoyl, etc.), $C_0$–$C_{10}$ sulfamoyl groups (e.g., sulfamoyl, methylsulfamoyl, phenylsulfamoyl, methane sulfonylsulfamoyl, etc.), $C_0$–$C_{10}$ amino groups (e.g., amino, dimethylamino, diethylamino, diethylaminoethylamino, morpholino, piperazino, etc.).

Specific examples of heterocyclic rings formed by $Z_3$ include 5- and 6-membered heterocyclic rings such as thiazolidine rings (e.g., thiazolidine, etc.), thiazoline rings (e.g., thiazoline, 4-methylthiazoline, etc.), benzothiazoline rings (e.g., benzothiazoline, 5-methoxybenzothiazoline, 6-methylbenzothiazoline, 5-chlorobenzothiazoline, 6-chlorobenzothiazoline, 6-methylbenzothiazoline, 6-hydroxybenzothiazoline, 6-tert-butylbenzothiazoline, 6-methoxybenzothiazoline, 5,6-methylenedioxybenzothiazoline, etc.), tetrahydrobenzothiazoline rings (e.g., 4,5,6,7-tetrahydrobenzothiazoline, etc.), naphthothiazoline rings (e.g., α-naphthothiazoline, β-naphthothiazoline, γ-naphthothiazoline, 5-methoxy-β-naphthothiazoline, 8-methoxy-α-naphthothiazoline, etc.), dihydroquinoline rings (e.g., 1,2-dihydroquinoline, 1,4-dihydroquinoline, 6-methyl-1,2-dihydroquinoline, etc. ), dihydropyridine rings (e.g., 1,2-dihydropyridine, 4-methylthio-1,2-dihydropyridine, 1,4-dihydropyridine, etc.), oxazolidine rings (e.g., oxazolidine, 4,4-dimethyloxazolidine, etc.), oxazoline rings (e.g., oxazoline, 4-phenyloxazoline, 4-methyloxazoline, etc.), benzoxazoline rings (e.g., benzoxazoline, 5-phenylbenzoxazoline, etc.), tetrahydrobenzoxazoline rings (e.g., 4,5,6,7-tetrahydrobenzoxazoline, etc.), naphthoxazoline rings (e.g., α-naphthoxazoline, β-naphthoxazoline, γ-naphthoxazoline, etc.), benzoselenazoline rings (e.g., benzoselenazoline, etc.), indolenine rings (e.g., 3,3-dimethylindolenine, etc.), imidazoline rings (e.g., 2-ethylimidazoline, etc.), benzimidazoline rings (e.g., benzimidazoline, 5,6-dichloro-2-ethylbenzimidazoline, 5-chloro-6-trifluoromethyl-2-ethylbenzimidazoline, etc.), dihydroisoquinoline rings (e.g., 1,2-dihydroisoquinoline, etc.), dihydronaphthothiazoline rings (e.g., 8,9-dihydronaphthothiazoline, etc.).

$Z_4$ represents, together with $N^+$ connected to $R_3$ group, an atomic group necessary to form a pyridinium ring, a thiazolium ring, a pyrimidinium ring, a benzothiazolium ring, a quinolinium ring, a naphthothiazolium ring, an oxazolidinium ring, an oxazolium ring, a benzoxazolium ring, a naphthoxazolium ring, an isoquinolinium ring, a benzoselenazolium ring, or an indolenium ring.

These heterocyclic rings may be substituted with one or more substituents or may be condensed with another ring, as described above for $Z_3$.

Specific examples of heterocyclic rings formed by $Z_4$ include 5- and 6-membered quarternized heterocyclic rings such as pyridinium rings (e.g., pyridinium, 4-methylthiopyridinium, 6-methylthiopyridinium, etc.), thiazolium rings (e.g., thiazolium, 4-methylthiazolium, 4-phenylthiazolium, etc.), pyrimidinium rings (e.g., pyrimidinium, etc.), benzothiazolium rings (e.g., benzothiazolium, 5-chlorobenzothiazolium, 6-chlorobenzothiazolium, 6-methoxybenzothiazolium, 6-acetylaminobenzothiazolium, 6-acetoxybenzothiazolium, etc.), quinolinium rings (e.g., quinolinium, 6-methylquinolinium, etc.), naphthothiazolium rings (e.g., α-naphthothiazolium, β-naphthothiazolium, γ-naphthothiazolium, etc.), oxazolidinium rings (e.g., oxazolidinium, etc.), oxazolium rings (e.g., oxazolium, 4-methyloxazolium, 4,5-diphenyl oxazolium, etc.), benzoxazolium rings (e.g., benzoxazolium, 5-phenylbenzoxazolium, etc.), naphthoxazolium rings (e.g., α-naphthoxazolium, β-naphthoxazolium, γ-naphthoxazolium, etc.), isoquinolinium rings (e.g., isoquinolinium, etc.), benzoselenazolium rings (e.g., benzoselenazolium, etc.), indolenium rings (e.g., 3,3-dimethylindolenium, etc.).

The alkyl group represented by $R_1$, $R_2$, and $R_3$ above can be a straight-chain, branched chain, or cyclic alkyl group and may be substituted. A preferred number of carbon atoms for the alkyl group represented by $R_1$, $R_2$, and $R_3$ is from 1 to 15 carbon atoms, more preferably 1 to 10 carbon atoms. Suitable examples of the alkyl group represented by $R_1$, $R_2$, and $R_3$ include methyl, ethyl, propyl, iso-propyl, butyl, iso-butyl, sec-butyl, tert-butyl, pentyl, hexyl, heptyl, octyl, cyclopropyl, cyclopentyl, cyclohexyl, 2-propenyl, 2-butenyl, 3-hexenyl. Specific examples of suitable substituents which can be present on the alkyl group when $R_1$, $R_2$, and $R_3$ represent a substituted alkyl group include one or more of halogen atoms such as chlorine, bromine, fluorine, and iodine, an alkyl group, an aryl group, an alkoxy group, a hydroxyl group, an amino group, a carboxyl group, and a cyano group, a sulfonyl group, a sulfamoyl group, a carbamoyl group, an acyl group, an alkoxycarbonyl group, an acyloxy group, and the like.

The aryl group represented by $R_1$, $R_2$, and $R_3$ above can be a monocyclic, bicyclic, or tricyclic aryl group such as a phenyl group, a biphenyl group, a naphthyl group or an anthracenyl group and such may be unsubstituted or substituted. Suitable examples of substituents which can be present on the aryl group represented by $R_1$, $R_2$, and $R_3$ include one or more of a halogen atom such as chlorine, bromine, fluorine, or iodine, an alkyl group, an alkoxy group, a hydroxyl group, a nitro group, a cyano group, an amino group, a sulfamoyl group, a carbamoyl group, a carboxyl group, an alkoxycarbonyl group, an acyl group, an acyloxy group, and the like. A suitable number of carbon atoms for the aryl group for $R_1$, $R_2$, and $R_3$ is 6 to 20, preferably 6 to 15.

Suitable examples of substituents which can be present on the $L_1$ and $L_2$ substituted methine group include an $C_1$–$C_5$ alkyl group (e.g., methyl, ethyl, butyl, etc.), an $C_6$–$C_{10}$ aryl group (e.g., phenyl, tolyl, etc.), a halogen atom (e.g., chlorine, bromine, fluorine and iodine), or an $C_1$–$C_5$ alkoxy group (e.g., methoxy, ethoxy, etc.).

The term "pharmaceutically acceptable anion" for X which is necessary for electrical charge balance in the compounds above is intended to mean an ion, when administered to the host subjected to the method of treatment of this invention, which is non-toxic and which renders the compounds above soluble in aqueous systems.

Suitable exmaples of pharmaceutically acceptable anions represented by X include halides such as chloride, bromide and iodine, sulfonates such as aliphatic and aromatic sulfonates, e.g., methanesulfonate, trifluoromethanesulfonate, p-toluenesulfonate, naphthalenesulfonate, 2-hydroxyethanesulfonate, and the like, sulfamates such as cyclohexanesulfamate, sulfates such as methyl sulfate and ethyl sulfate, bisulfates, borates, alkyl and dialkyl phosphates such as diethyl phosphate and methylhydrogen phosphate, pyrophsophates such as trimethylpyrophosphate and diethyl hydrogen pyrophosphate, carboxylates, advantageously carboxy- and hydroxy-substituted carboxylates and carbonates. Preferred examples of pharmaceutically acceptable anions include chloride, acetate, propionate, valerate, citrate, maleate, fumarate, lactate, succinate, tartrate and benzoate.

Among the compounds having the general formulae (II) to (III), further preferred are those compounds represented by the following formulae (IIA), (IIB), (IIC), (IIIA), (IIIB) and (IIIC).

Formula (IIA):

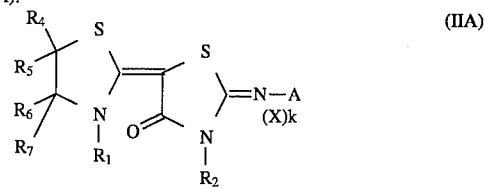

Formula (IIB):

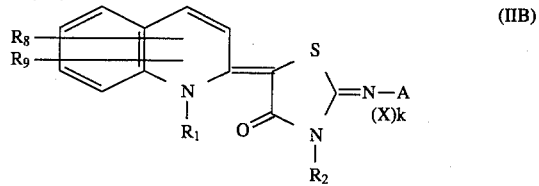

Formula (IIC):

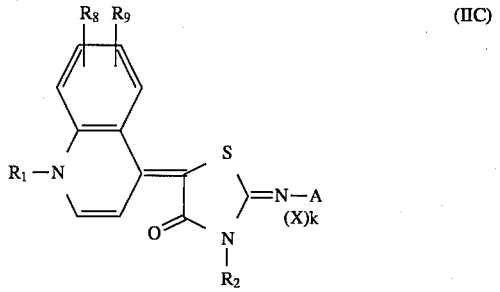

Formula (IIIA):

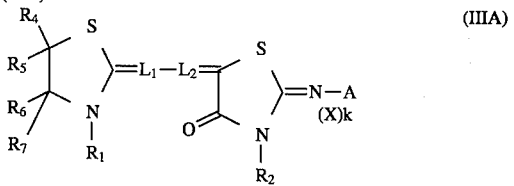

Formula (IIIB):

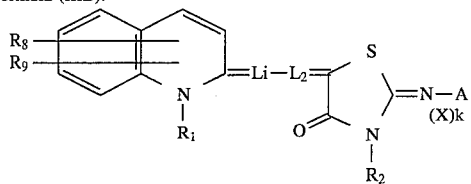

Formula (IIIC):

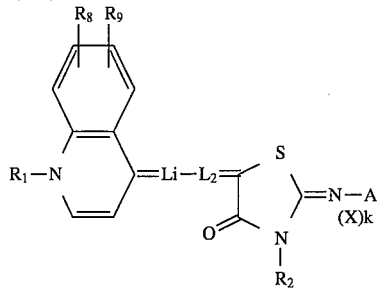

wherein $R_4$, $R_5$, $R_6$, and $R_7$, which may be the same or different, each represents such substituents as defined for those on $Z_3$, or two of $R_5$ and $R_6$ may combine and form a single bond, moreover two of $R_4$ and $R_7$ may combine and form a 5- or 6-membered fused ring such as a thiophene ring, a benzene ring, a naphthalene ring, and the like.

$R_8$ and $R_9$, which may be the same or different, each represents such substituents as defined for those on $Z_3$.

$R_1$, $R_2$, k and X have the same meanings as defined above.

A represents

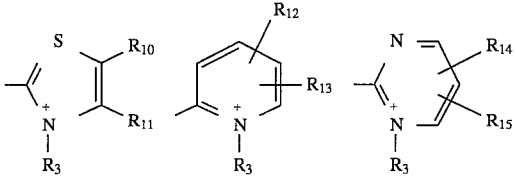

wherein $R_3$ has the same meaning as defined above.

$R_{10}$, $R_{11}$, $R_{12}$, $R_{13}$, $R_{14}$, and $R_{15}$ which may be the same or different, each represents such substituents as defined for those on $Z_3$, or two of $R_{10}$ and $R_{11}$, or $R_{12}$ and $R_{13}$ may combine and form a 5- or 6-membered fused ring such as a thiophene ring, a furan ring, a benzene ring, a naphthalene ring, and the like.

The compounds of General Formulas (I) to (III) described above can be easily produced from known starting materials in accordance with the methods disclosed in British Patent Nos. 489,335 and 487,051; in U.S. Pat. Nos. 2,388,963, 2,454,629 and 2,504,468; in E. B. Knott et al, J. Chem. Soc., 4762 (1952) and in E. B. Knott, J. Chem. Soc., 949 (1955), the disclosure of which is incorporated herein by reference.

Typical examples of compounds of General Formulas (I) to (III) which can be employed in this invention include the following compounds; however, the present invention is not to be construed as being limited to these compounds.

I-1

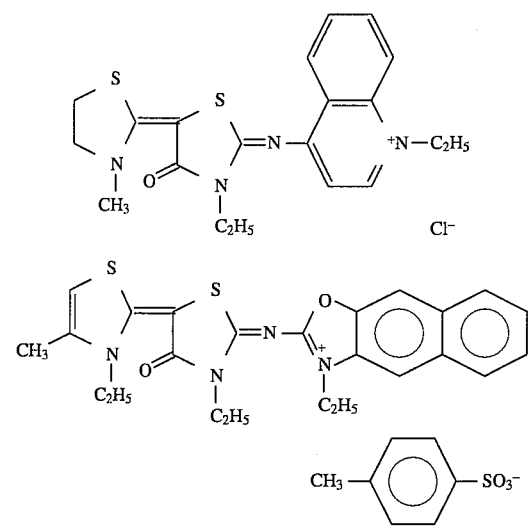

I-2

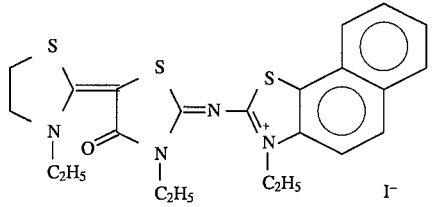

I-3

I-4

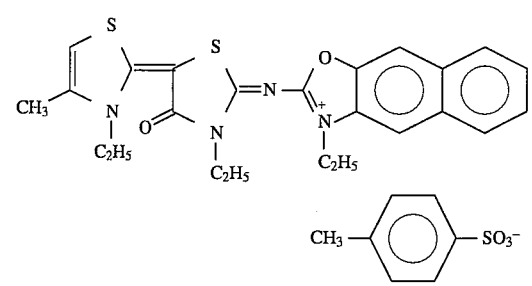
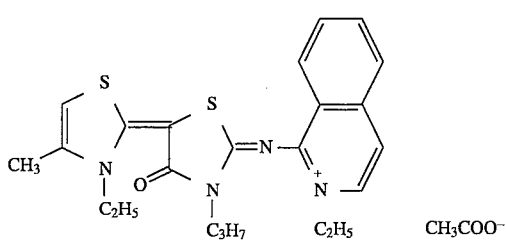

I-5

I-6

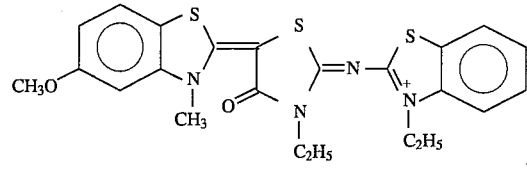
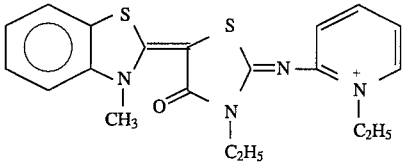

I-7

I-8

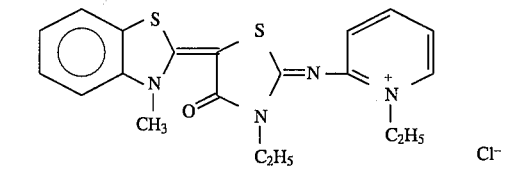
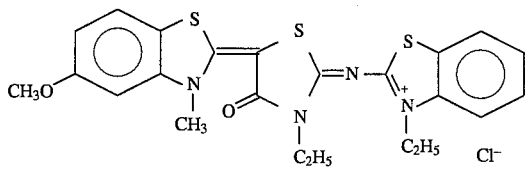

-continued
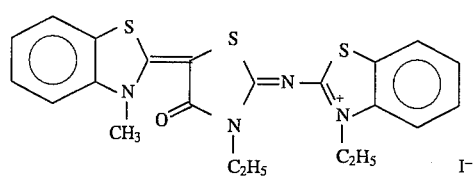 I-9 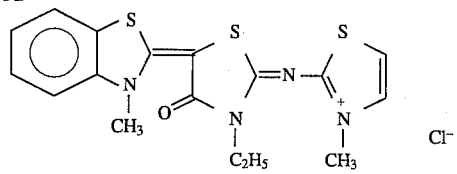 I-10
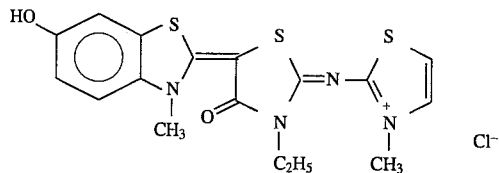 I-11 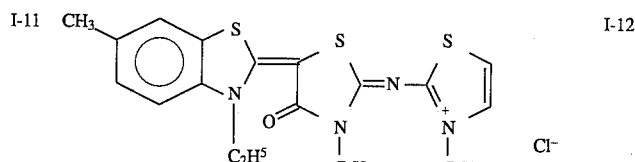 I-12
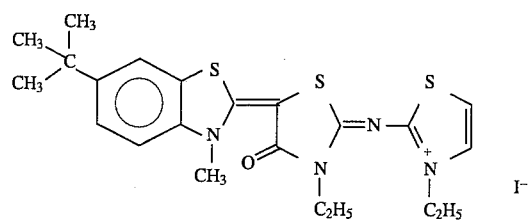 I-13 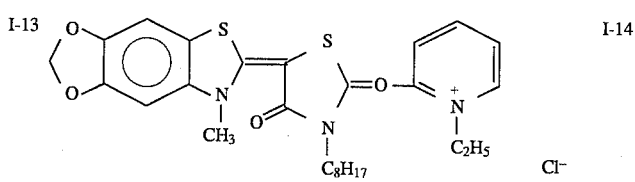 I-14
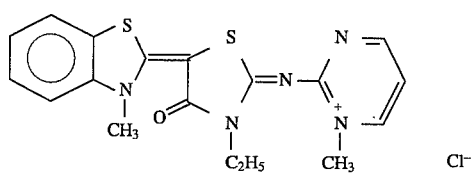 I-15 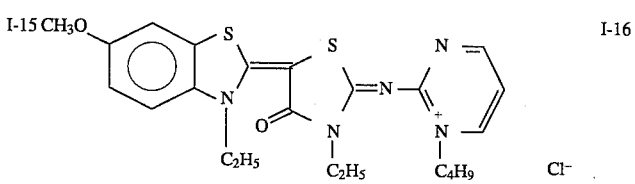 I-16
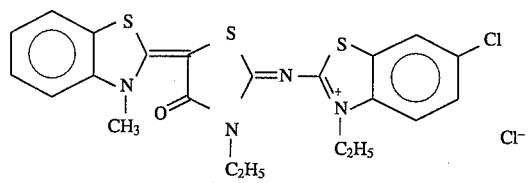 I-17 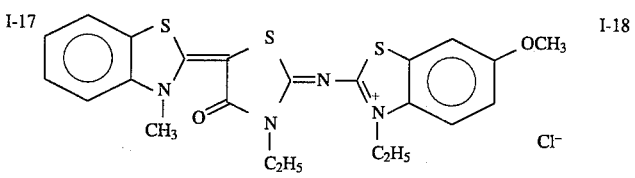 I-18
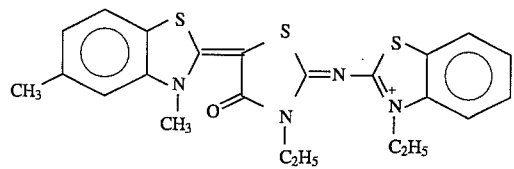 I-19 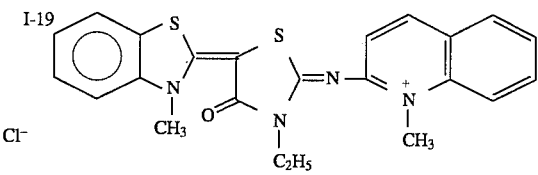 I-20
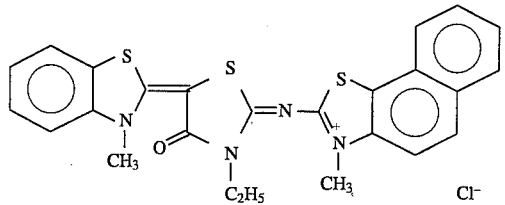 I-21 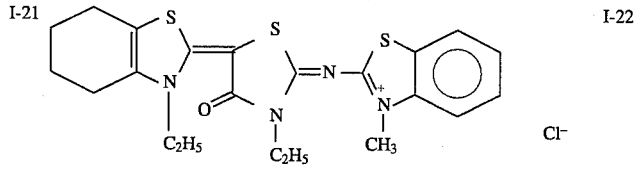 I-22
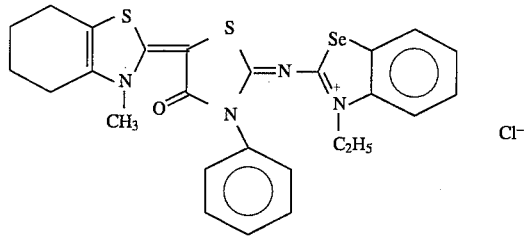 I-23 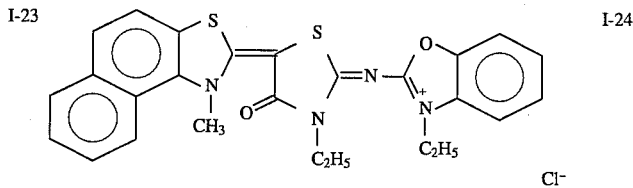 I-24

-continued
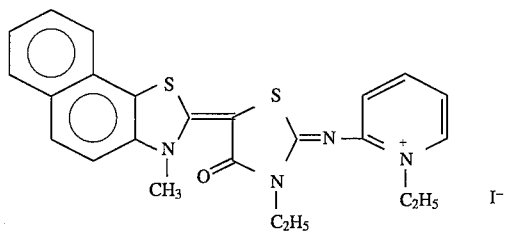
I-25
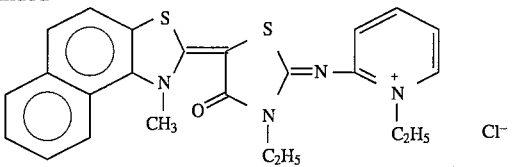
I-26
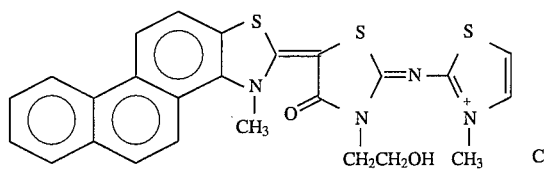
I-27
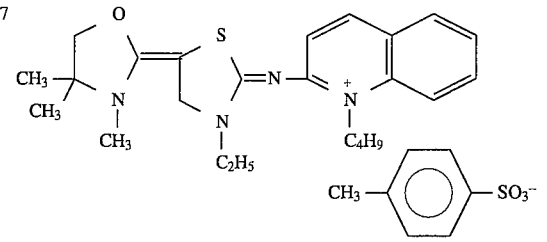
I-28
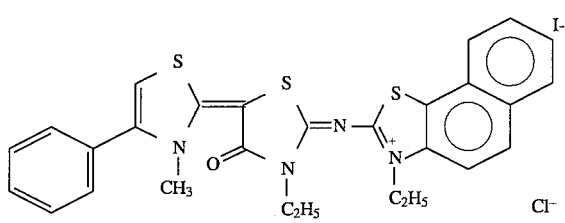
I-29
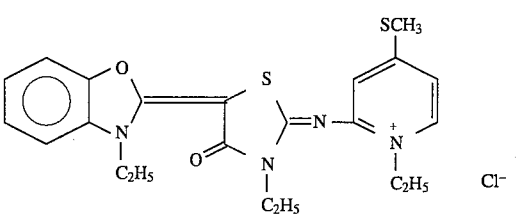
I-30
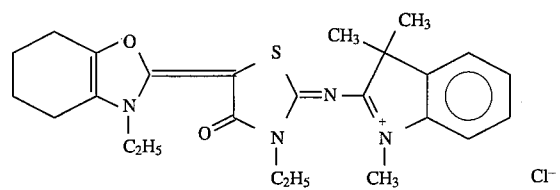
I-31
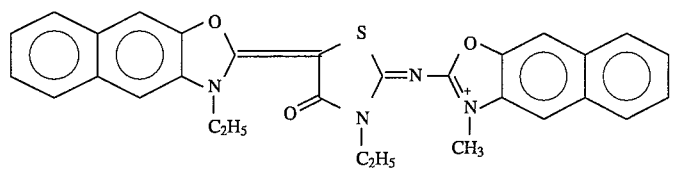
I-32
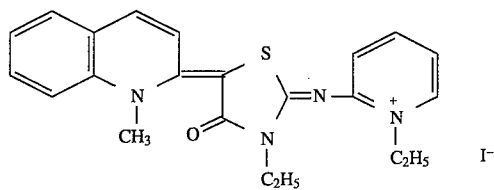
I-33
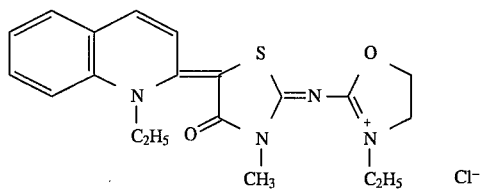
I-34
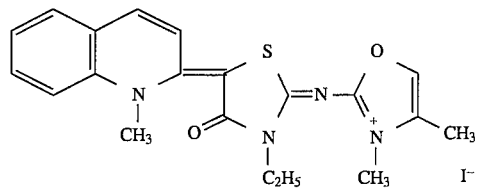
I-35
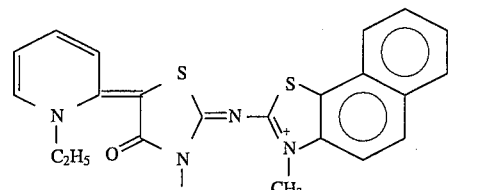
I-36
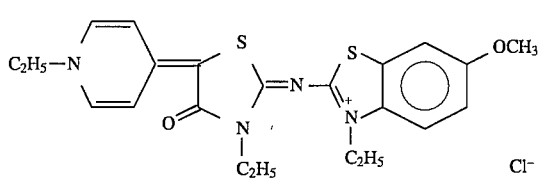
I-37
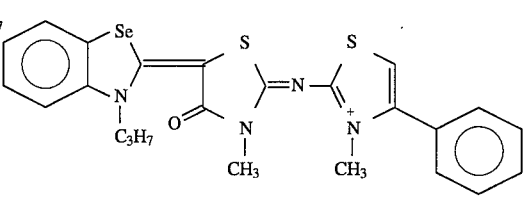
I-38

-continued
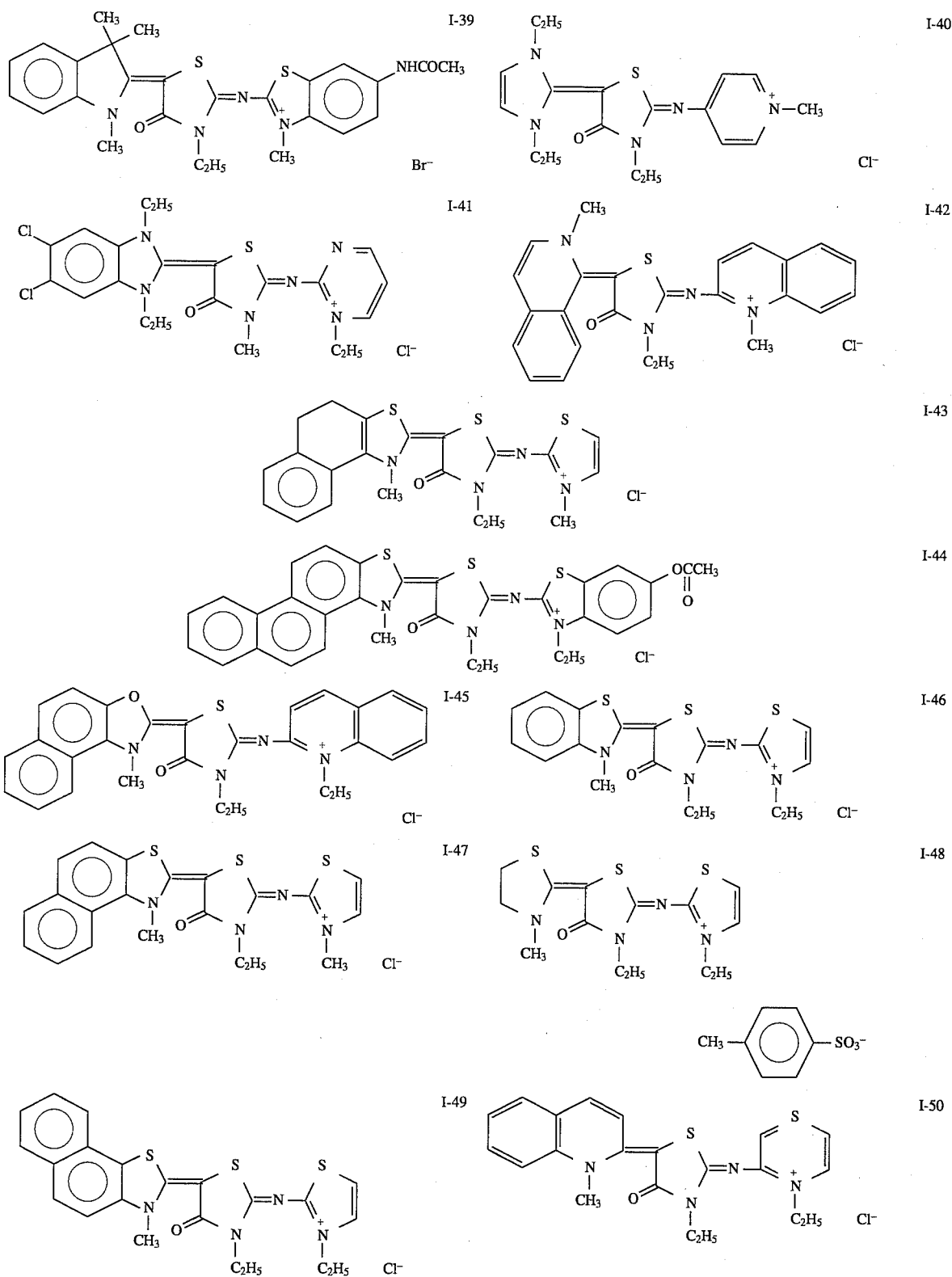

-continued
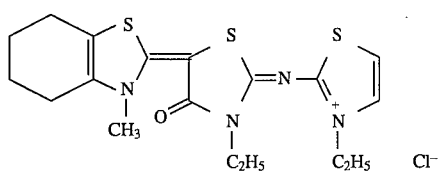
I-51
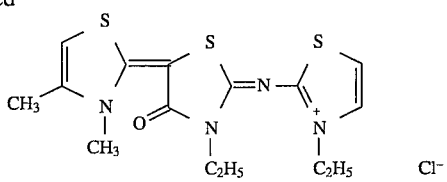
I-52
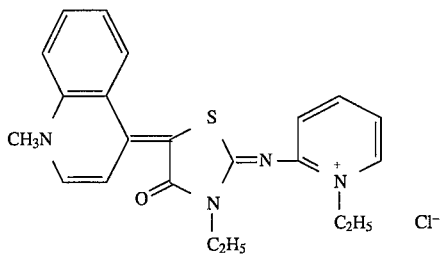
I-53
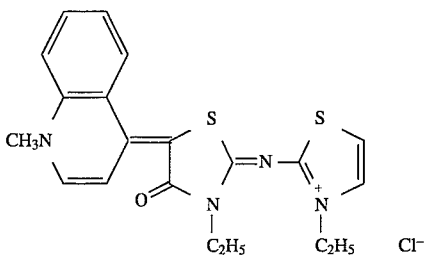
I-54
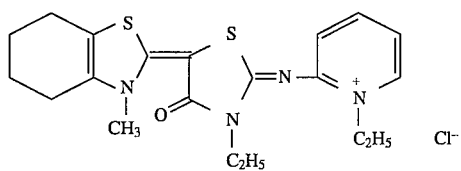
I-55
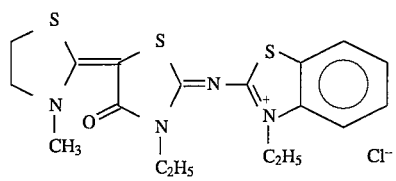
I-56
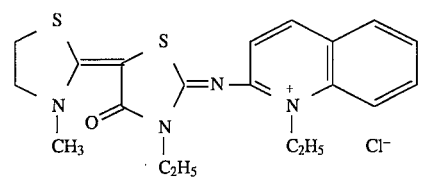
I-57
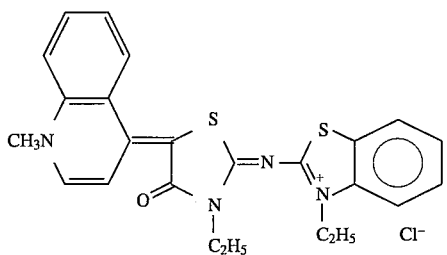
I-58
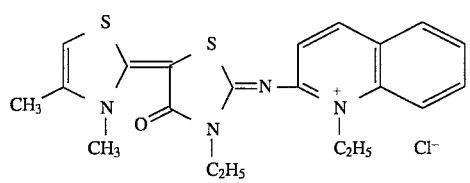
I-59
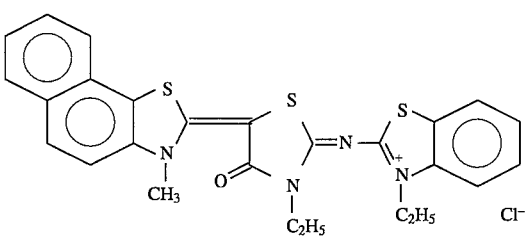
I-60
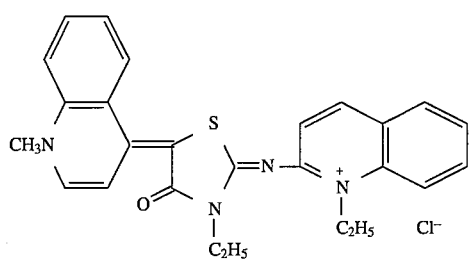
I-61
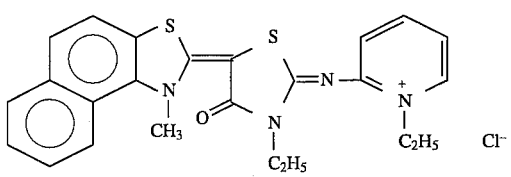
I-62
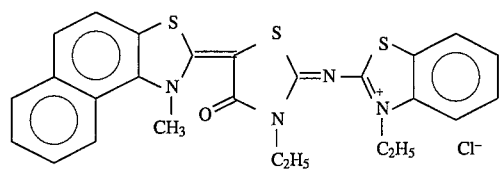
I-63
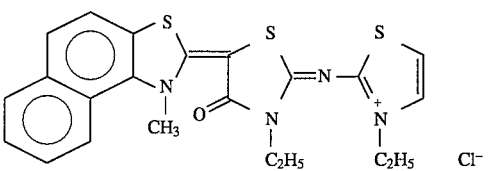
I-64

-continued
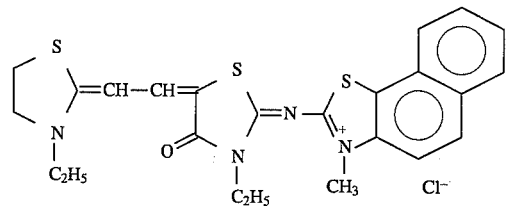
II-1
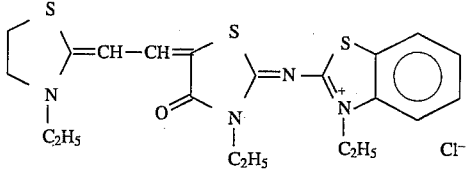
II-2
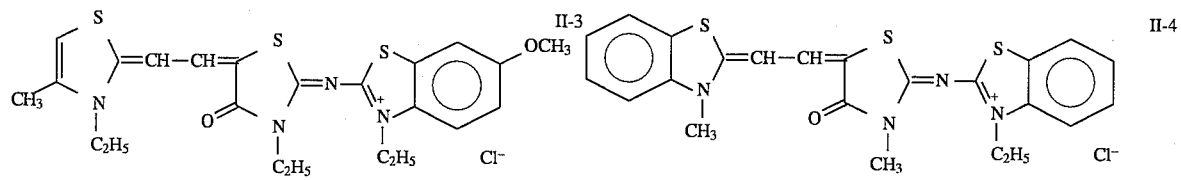
II-3  II-4
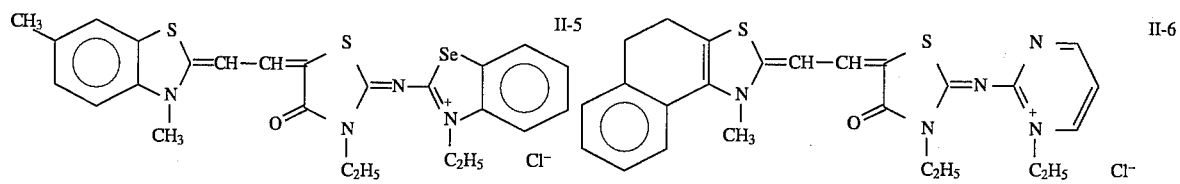
II-5  II-6
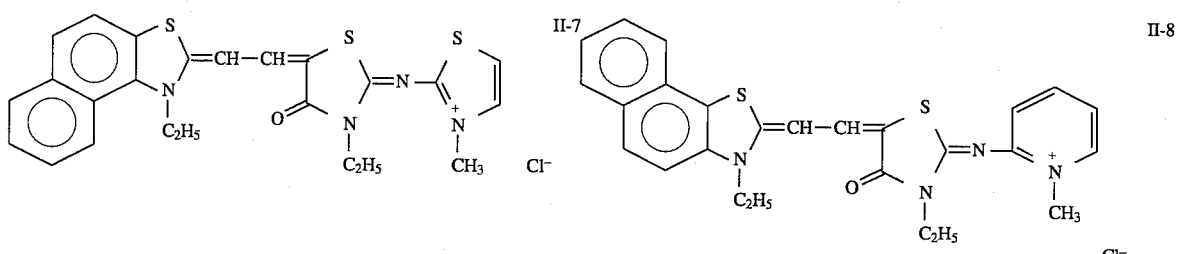
II-7  II-8
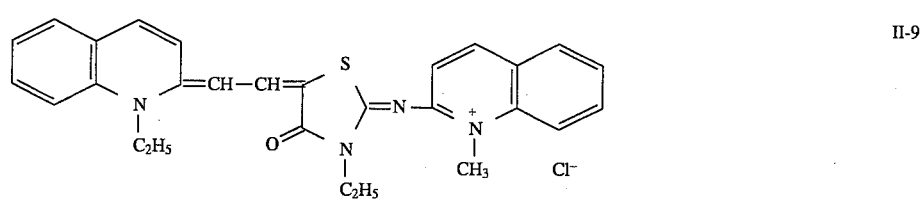
II-9
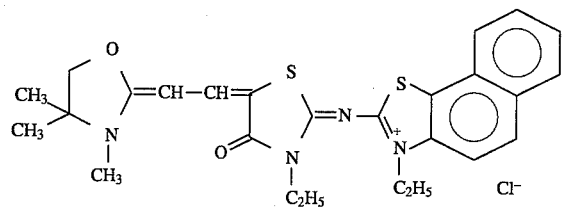
II-10
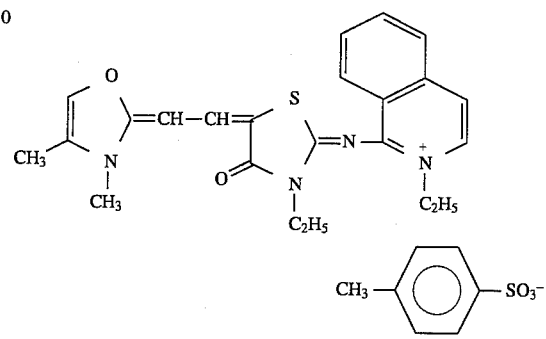
II-11
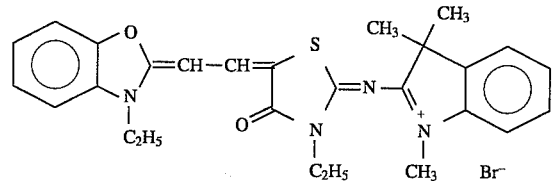
II-12

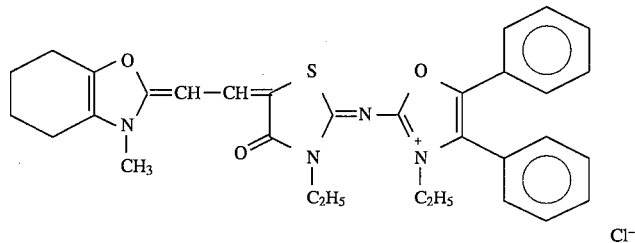
II-13
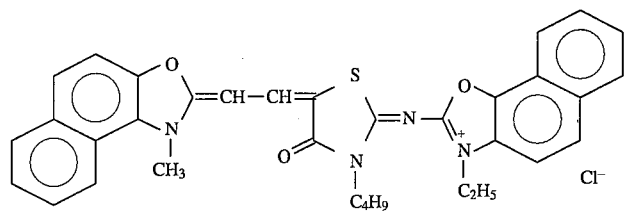
II-14
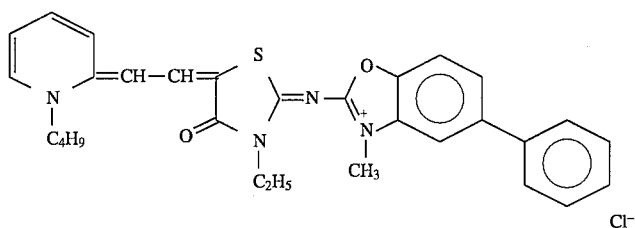
II-15
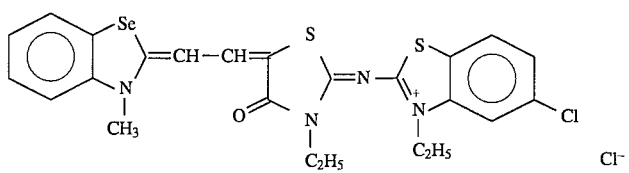
II-16
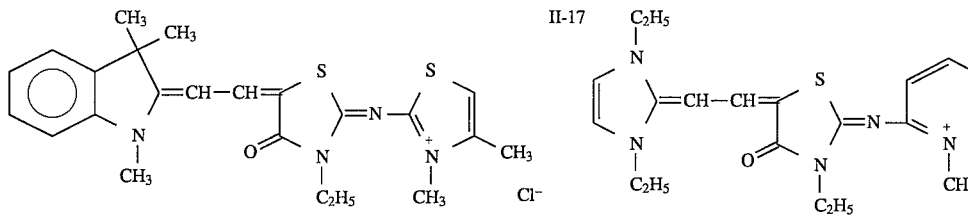
II-17  II-18
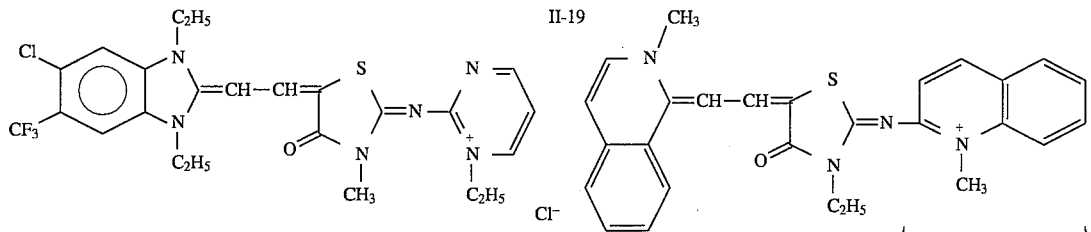
II-19  II-20
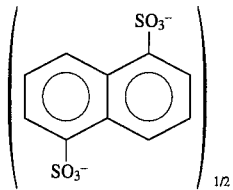
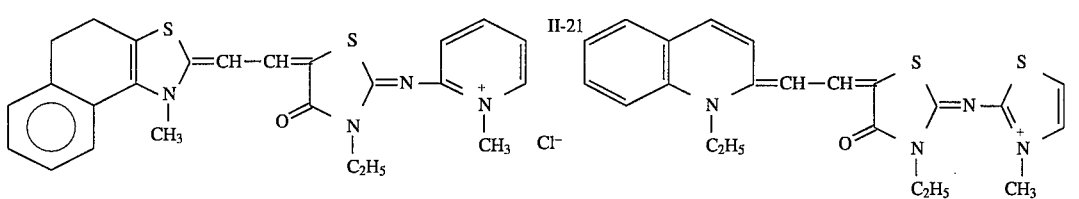
II-21  II-22

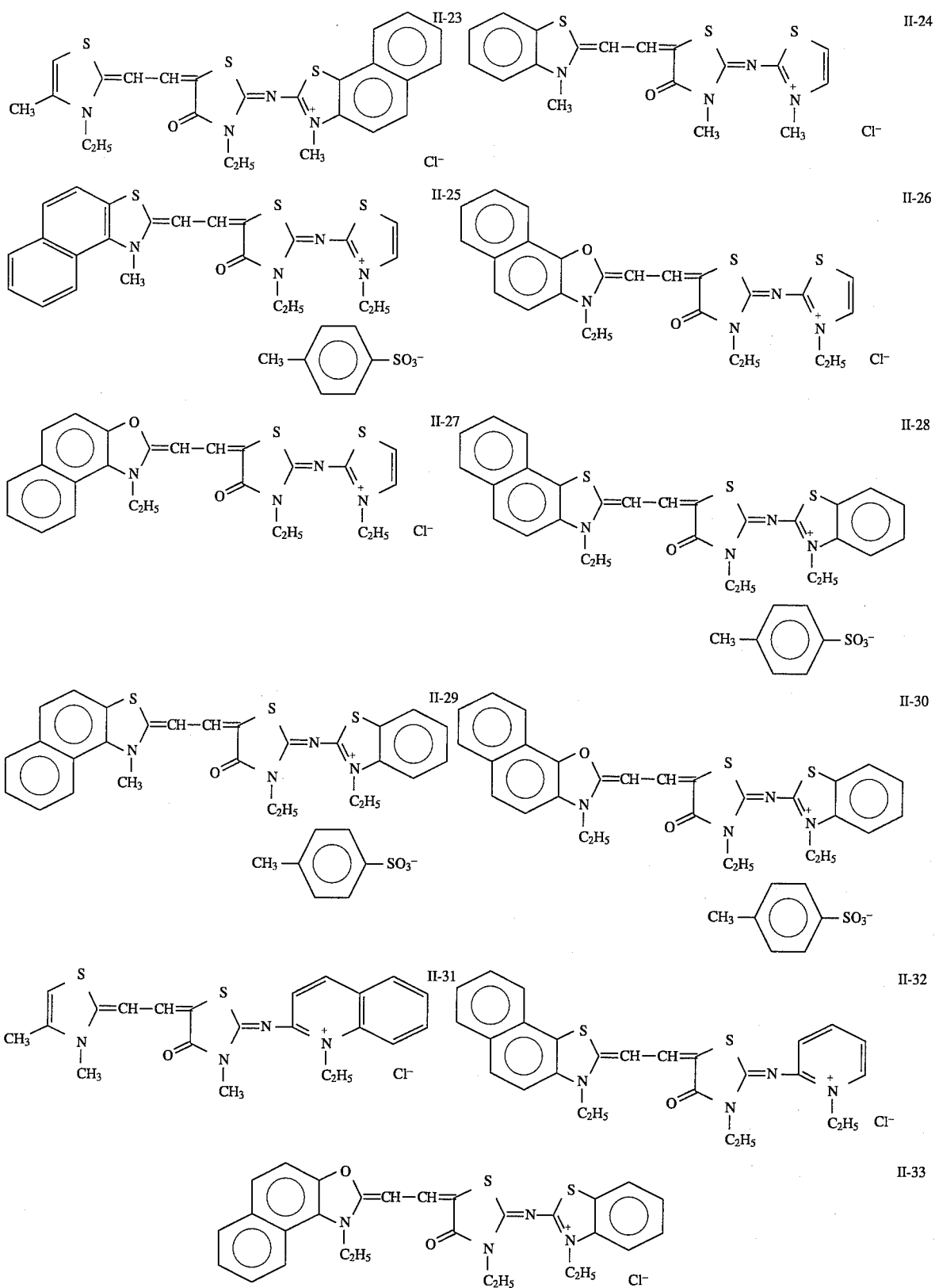

SYNTHESIS EXAMPLE 1 (Compound I-6)

1) Preparation of 3-ethyl-5-(3-methylbenzothiazolin-2-ylidene)thiazolidine-4-one-2-thione In a 3L three-necked flask fitted with a reflux condenser were placed 400 g of 2-methylthiobenzothiazole, 616 g of methyl p-toluenesulfonate, and 560 ml of anisole. The mixture was heated at 120° C. for 4 hours, then cooled to room temperature.

To the resulting mixture was added 8 L of acetonitrile, and the mixture was stirred at room temperature for 15 minutes then poured into a 10 L three-necked flask. To the mixture was added 354 g of 3-ethylthiazolin-4-one-2-thione, and the solution was cooled to 5° C. One half liter of triethylamine was added dropwise over a period of 30 minutes at 10° C., and the resulting mixture was stirred for four hours at 10° C. The yellow precipitates were filtered under reduced pressure, washed first with 0.4 L of acetonitrile, and then 1.4 L of methanol to give 800 g of the crude product.

In a 10 L three-necked flask fitted with a reflux condenser were placed the crude product, 2.1 L of acetone and 4.2 L of methanol. The mixture was stirred under reflux for 15 minutes. After cooling to 25° C., the resulting mixture was filtered under reduced pressure, washed with 1.4 L of methanol, and dried at 60° C. for 20 hours.

Yield: 89.3%

2) Preparation of 3-ethyl-5-(3-methylbenzothiazolin-2-ylidene)-2-methylthio-4-oxo-2-thiazolium p-toluenesulfonate In a 10 L three-necked flask fitted with a reflux condenser were placed 750 g of 3-ethyl-5-(3-methylbenzothiazolin-2-ylidene)thiazolin-4-one-2-thione, 1360 of methyl p-toluenesulfonate, and 0.75 L of dimethylformamide (DMF). This mixture was allowed to warm to 130° C. This temperature was maintained for 2.5 hours and the mixture was stirred for constantly. At the end of 2.5 hours, the mixture was cooled to 95° C. and 6.5 L of acetone was added. After cooling to 25° C., the precipitate was filtered under reduced pressure and washed with 2 L of acetone.

This crude product and 5.2 L of acetone were placed in a 10 L three-necked flask fitted with a reflux condenser. The mixture was stirred under reflux for 15 minutes and cooled to 25° C. The precipitates were filtered under reduced pressure and washed with 2 L of acetone. The product was dried at 50° C. for 20 hours.

Yield: 92.3%

3) Preparation of 2-amino-1-ethylpyridinium iodide

In a 1 L three-necked flask fitted with a reflux condenser were placed 28.2 g of 2-aminopyridine and 60.8 g of iodoethane, and the mixture was stirred under reflux for 2 hours. The reaction mixture was stirred at room temperature for another hour, and the resulting precipitate was filtered under reduced pressure and washed with ethyl acetate (50 ml×2). The residue was dried at room temperature for 3 hours.

Yield; 68.2 g

4) Preparation of 1-ethyl-2-{[3-ethyl-5-(3-methylbenzothiazolin-2-ylidene)]-4-oxothiazolin-2-ylideneamino}pyridinium iodide (Compound I-6)

In a 2 L of three-necked flask were placed 24.7 g of 3-ethyl-5-(3-methylbenzothiazolin-2-ylidene)-2-methylthio-4-oxo-2-thiazolium p-toluenesulfonate, 12.5 g of 2-amino-1-ethylpyridinium iodide, and 500 g of acetonitrile, and the mixture was stirred at 50° C. To the resulting solution was added 20.2 g of triethylamine and the mixture was stirred at the same temperature for additional 1.5 hours. The reaction mixture was cooled to room temperature and the precipitates were filtered under reduced pressure and washed with acetonitrile (50 ml×2). The crude product was dissolved in 250 ml of chloroform/methanol (1:1) and to this solution was added 400 ml of ethyl acetate. The precipitates were filtered under reduced pressure, washed with ethyl acetate (100 ml×2), and dried under reduced pressure at room temperature to give the compound I-6.

Yield: 8.8 g mp: 275°–276° C.

SYNTHESIS EXAMPLE 2 (Compound I-7)

One gram of the compound I-6 was dissolved in 50 ml of chloroform/methanol (1/1), and the solution was passed through the strongly basic anion exchange resin column (Amberlyst A-26, ORGANO/eluent: methanol). The eluent was combined and filtered with a microfilter (0.2 μm), and the filtrate was concentrated under reduced pressure. The residue was dissolved in ethanol and ethyl acetate was added to the solution. The precipitates were filtered under reduced pressure, washed with ethyl acetate, and dried under reduced pressure to give the compound I-7.

Yield: 0.8 g mp: 242°–244° C.

SYNTHESIS EXAMPLE 3 (Compound I-33)

In a 200 mL three-necked flask were placed 2.5 g of 3-ethyl-2-methylthio-5-(1-methylquinoline-2-ylidene)-4-oxo-2-thiazolium p-toluenesulfonate, 1.3 g of 2-amino-1-ethylpyridinium iodide, and 50 ml of acetonitrile, and the mixture was stirred at 50° C. To this solution was added dropwise 2.8 ml of triethylamine, and the mixture was stirred at the same temperature for additional 2 hours, treated as the compound I-6 to give the compound I-33.

Yield: 1.2 g mp: 233°–234° C.

SYNTHESIS EXAMPLE 4 (Compound I-10).

1) Preparation of 2-amino-3-methylthiazolium p-toluenesulfonate

In a 200 ml three-necked flask were placed 2.0 g of 2-aminothiazole and 5.6 g of methyl p-toluenesulfonate, and the mixture was stirred at 120° C. for 4 hours. After the resulting mixture was cooled to 60° C., 100 ml of acetone was added and the mixture was stirred for 1 hour. The precipitates were filtered under reduced pressure, washed with acetone, and dried at room temperature under reduced pressure.

Yield: 5.4 g

2) Preparation of Compound I-10

In a 200 ml three-necked flask were placed 2.5 g of 3-ethyl-5-(3-methylbenzothiazolin-2-ylidene)-2-methylthio-4-oxo-2-thiazolium p-toluenesulfonate, 1.4 g of 2-amino-3-methylthiazolium p-toluenesulfonate and 30 ml of acetonitrile, and the mixture was stirred at 60° C. To this solution was added dropwise 2.2 ml of triethylamine, and the mixture was stirred at the same temperature for 30 minutes. After the resulting mixture was cooled to room temperature, the precipitate was filtered under reduced pressure and washed with acetonitrile. The crude product was dissolved in 50 ml of methylene chloride/methanol (1/1) and 10 ml of acetonitrile, and the solution was concentrated to one fifth under reduced pressure. After the residue was left at room temperature for 2 hours, the crystal was filtered under reduced pressure. The crystals were further treated with the strongly basic anion exchange resin column (PA-318/eluent: methanol) to give the compound I-10.

Yield: 1.5 g
mp: 253°–254° C.

SYNTHESIS EXAMPLE 5 (Compound I-15)

1) Preparation of 2-amino-1-methylpyrimidinium p-toluenesulfonate

In a 200 ml three-necked flask were placed 1.8 g of 2-aminopyrimidine and 5.6 g of methyl p-toluenesulfonate, and the mixture was stirred at 120° C. for 3 hours. After the resulting mixture was cooled to 60° C., 100 ml of acetone was added and the mixture was stirred at room temperature for 1 hour. The crystals were filtered under reduced pressure, washed with acetone, and dried at room temperature under reduced pressure.

Yield: 5.9 g

2) Preparation of Compound I-15

Using 2.5 g of 3-ethyl-5-(3-methylbenzothiazolin-2-ylidene)-2-methylthio-4-oxo-2-thiazolium p-toluenesulfonate, and 1.4 g of 2-amino-1-methylpyrimidinium p-toluenesulfonate, on the same method as that of the compound I-10, gave the compound I-15.

Yield: 1.8 g
mp: 248°–250° C.

SYNTHESIS EXAMPLE 6 (Compound I-47)

In a 200 ml three-necked flask were placed 3.1 g of 3-ethyl-5-(3-methylnaphtho [1,2-d] thiazolin-2-ylidene)-2-methylthio-4-oxo-2-thiazolium p-toluenesulfonate, 1.4 g of 2-amino-3-methylthiazolium p-toluenesulfonate, and 30 ml of acetonitrile, and the mixture was stirred at 70° C. To this solution was added dropwise 2.2 ml of triethylamine and the mixture was further stirred at the same temperature for 1 hour. To the resulting mixture was added 100 ml of acetone and the mixture was stirred at room temperature for 1 hour. The crystals were filtered under reduced pressure and washed with acetone. The crude crystals were recrystallized from chloroform-methanol and treated with a strongly basic anion exchange resin column to give the compound I-50.

Yield: 1.1 g
mp: 229°–231° C.

SYNTHESIS EXAMPLE 7 (Compound II-3)

1) Preparation of 2-amino-3-ethyl-6-methoxybenzothiazolium p-toluenesulfonate

In a 200 ml three-necked flask were placed 3.6 g of 2-amino-6-methoxybenzothiazole and 6.0 g of ethyl p-toluenesulfonate, and the mixture was stirred at 120° C. for 3 hours. To the resulting mixture was added acetone and the mixture was stirred at room temperature for 1 hour. The crystals were filtered under reduced pressure and washed with acetone to give the desired compound.

Yield: 6.3 g

2) Preparation of Compound II-3

In a 200 ml three-necked flask were placed 1.50 g of 3-ethyl-5-{2-(3-ethyl-4-methylthiazolin-2-ylidene)ethylidene}-3-methylthio-4-oxothiazolium p-toluenesulfonate, 1.14 g of 2-amino-3-ethyl-6-methoxybenzothiazolium p-toluenesulfonate and 18 ml of acetonitrile, and the mixture was stirred at 70° C. for 2.5 hours. To the resulting mixture was added 50 ml of acetone and 50 ml of ethyl acetate and the mixture was stirred for an additional hour. The crystals were filtered under reduced pressure and washed with ethyl acetate. The crystal was recrystallized from chloroform-methanol and treated with a strongly basin anion exchange resin column (DIAION, PA-318) to give the compound II-3.

Yield: 0.3 g
mp: 170°–173° C.

Other compounds listed on examples were synthesized on the same method as above.

The pharmaceutical compositions of this invention containing one or more compounds of the General Formulas (I) to (III) described above can be effectively used to treat various types of cancer including melanomas, hepatomas, gliomas, neuroblastomas, sarcomas and carcinomas of the lung, colon, breast, bladder, ovary, testis, prostate, cervix, pancreas, stomach, small intestine and other organs.

The pharmaceutical compositions of this invention can contain one or more compounds of the General Formulas (I) to (III) described above and, if desired, can be employed in combination with other therapeutic agents including conventional anti-tumor agents known in the art. Suitable examples of such conventional anti-tumor agents which can be used include adriamycin, cisplatin, colchicine, CCNU (Lomastine), BCNU (Carmustine), Actinomycin D, 5-fluorouracil, thiotepa, cytosinearabinoside, cyclophosphamide, mitomycin C, and the like.

Suitable examples of pharmaceutical carriers or diluents which can be employed in the pharmaceutical composition of this invention in combination with the compound of the General Formulas (I) to (III) include glucose, sucrose, lactose, ethyl alcohol, glycerin, mannitol, sorbitol, pentaerythritol, diethylene glycol, triethylene glycol, ethylene glycol, propylene glycol, dipropylene glycol, polyethylene glycol 400, other polyethylene glycols, mono-, di- and triglycerides of saturated fatty acids such as glyceryl trilaurate, glyceryl monostearate, glyceryl tristearate and glyceryl distearate, pectin, starch, alginic acid, xylose, cyclodextrins or derivatives thereof talc, lycopodium, oils and fats such as olive oil, peanut oil, castor oil, corn oil, wheat germ oil, sesame oil, cottonseed oil, sunflower seed oil and cod-liver oil, gelatin, lecithin, silica, cellulose, cellulose dereivatives such as methyl hydroxypropyl cellulose, methyl cellulose, hydroxyethyl cellulose, magnesium and calcium salts of fatty acids with 12 to 22 carbon atoms such as calcium stearate, calcium laureate, magnesium oleate, calcium palmirate, calcium behenate and magnesium stearate, emulsifiers, esters of saturated and unsaturated fatty acids, e.g., having 2 to 22 carbon atoms, especially 10 to 18 carbon atoms, with monohydric aliphatic alcohols (e.g., having 1 to 20 carbon atoms such as alkanols) or polyhydric alcohols such as glycols, glycerine, diethylene glycol, pentaerythritol, ethyl alcohol, butyl alcohol, octadecyl alcohol and silicones such as dimethyl polysiloxane. Additional carriers conventionally used in pharmaceutical compositions may also be appropriate for this invention.

The pharmaceutically effective amount of the compound of the General Formulas (I) to (III) which can be employed and the mode or manner of administration will be dependent upon the nature of the cancer, the therapy sought, the severity of the disease, the degree of malignancy, the extent of metastatic spread, the tumor load, general health status, body weight, age, sex, and the (genetic) racial background of the patient. However, in general, suitable modes of administration include intravenous, intraperitoneal, intramuscular or intravesicular injection in the form of, for example, a compound of the General Formulas (I) to (III) in, e.g., a 5% glucose aqueous solution or with other appropriate carriers or diluents as described above. A suitable therapeutically effective amount of a compound of the General Formulas (I) to (III) in the composition is about 0.01% by weight to about 10% by weight, more generally 0.1% by weight to about 1%, based on the weight of the composition.

Again, as noted above, pharmaceutically effective amounts will be generally determined by the practitioner based on the clinical symptoms observed and degree of progression of disease and like factors but a suitable therapeutically effective amount of the compound of the General Formulas (I) to (III) generally can range from 10 mg to 500 mg, more generally 100 mg to 200 mg, administered per day per 70 kg of body weight, in single or multiple doses, as determined appropriate for the therapy involved.

In order to demonstrate the effectiveness of the compounds of the General Formulas (I) to (III) and the pharmaceutical compositions and method of this invention, the following examples are given to demonstrate effectiveness and selectivity values for a number of the compounds of the initial General Formulas (I) to (III) employed in the composition and method of this invention as well as compounds for comparison. The results obtained are shown in the tables below.

EXAMPLE 1

The data obtained in Table I below were obtained in the following manner.

Human colon carcinoma cell line CX-1 or normal monkey kidney epithelial cell line CV-1 was chosen as representatives of cancer cells and normal cells, respectively. This assay demonstrates the selective killing of cancer cells by compounds of the General Formulas (I) to (III). CX-1 cells (2,000 cells/well) and CV-1 cells (1,000 cells/well) were plated in 24-well plastic culture plates. Compounds of General Formulas (I) to (III) were dissolved in dimethylsulfoxide at a concentration of 1 mg/ml and serial dilutions of this solution in cell culture media at concentrations varying from 20 µg/ml to 0.0025 µg/ml were added to individual wells. The control received culture media only. Cells were treated with compounds of General Formulas (I) to (III) at 37° C. for 24 hours. After rinsing with fresh culture medium three times, the cells were further incubated at 37° C. for 7 to 10 days. Cell colonies were fixed and stained with 2% crystal violet in 70% ethanol for 10 minutes and rinsed in water. The number of colonies in each well were counted and the concentration of compounds at which the colony number was reduced to 50% of the control ($IC_{50}$) was determined. The selectivity is defined as the ratio of $IC_{50}$ for CV-1 and $IC_{50}$ for CX-1.

TABLE I

| Compound No. | CV-1 ($IC_{50}$) µg/ml | CX-1 ($IC_{50}$) µg/ml | Selectivity |
|---|---|---|---|
| A | 0.6 | 0.03 | 20 |
| B | <0.1 | 0.05 | <2 |
| C | 2 | 0.04 | 50 |
| D | 1.5 | 0.03 | 50 |
| E | 6 | 0.5 | 12 |
| F | 1.5 | 0.03 | 50 |
| G | 0.1 | 0.02 | 5 |
| H | 0.1 | 0.04 | 2.5 |
| I-10 | >20 | 0.08 | >250 |
| I-19 | 6 | 0.05 | 120 |
| I-25 | 10 | 0.1 | 100 |
| II-7 | 4 | 0.03 | 133 |

Compounds A, B, C, D, E, F, G and H used for comparison were as follows:

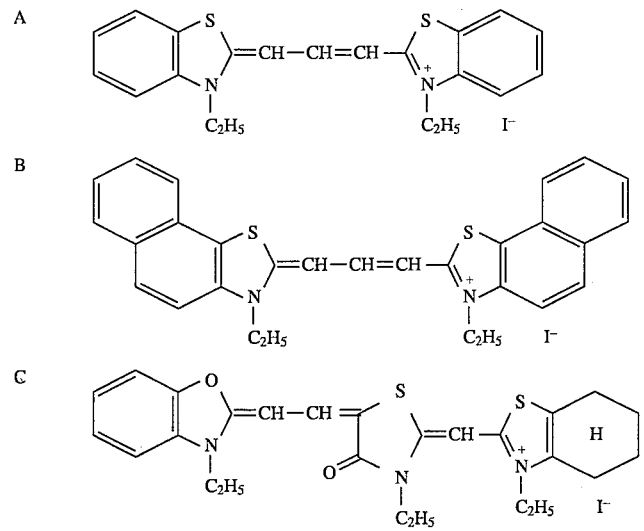

-continued

| Compound No. | Structural Formula |
|---|---|

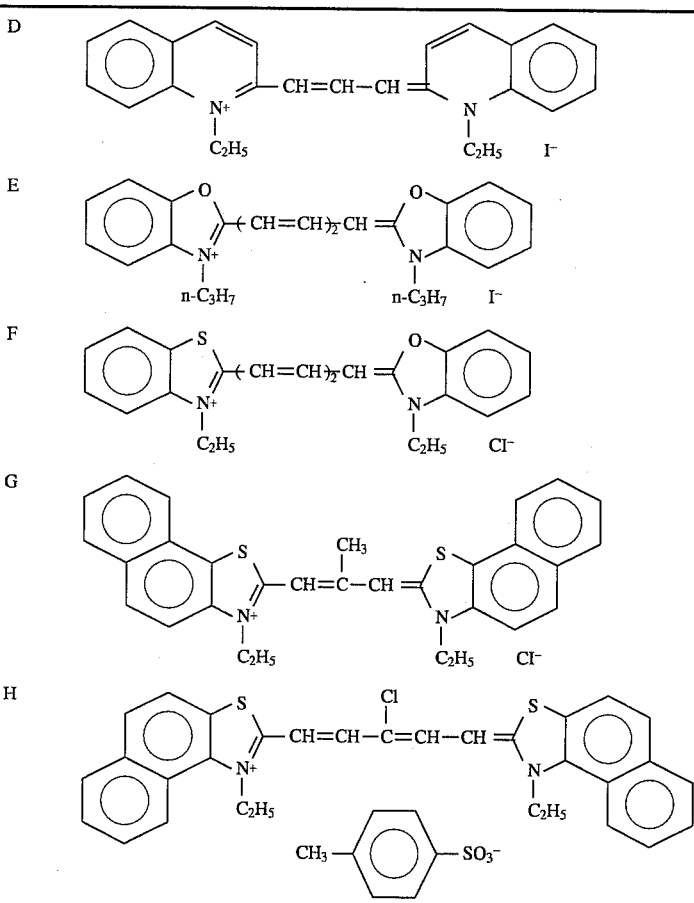

From the results set forth in Table I above, it is very clear that the compounds of the General Formulas (I) to (III) used in this invention have distinctively high selectivity values in comparison with Compounds A, B, C, D, E, F, G and H for comparison.

Based on information available in the literature, Compounds A and B with a selectivity of 20 and <2, respectively, would be highly toxic to animals and, therefore, humans. Indeed, it has been found that A and B are highly toxic to normal nude mice. Although Compounds C, D, E and F are less toxic to normal nude mice, because of its lower selectivity compared with other compounds of General Formulas (I) to (III), it is expected to have lower efficacy in treating cancers in animals as well as humans. Compounds G and H with a selectivity of 5 and 2.5, respectively, would be highly toxic to animals and, therefore, humans. Indeed, it has been found that compounds G and H are highly toxic to normal nude mice.

EXAMPLE 2

To further demonstrate the uniqueness of the present invention, compounds of the General Formulas (I) to (III) were tested using the protocol described in Example 1 except that the KB cell was used instead of the human colon carcinoma cell line CX-1. The selectivity values, KB cell values and CV-1 values for compounds of the present invention are shown in Table II below.

TABLE II

| Compound No. | CV-1 (IC$_{50}$) µg/ml | KB Cell (IC$_{50}$) µg/ml | Selectivity |
|---|---|---|---|
| I-18 | 26.5 | 0.15 | 177 |
| I-25 | 30 | 0.17 | 176 |
| I-33 | 30 | 0.39 | 77 |
| I-46 | 27.4 | 0.083 | 330 |
| I-47 | 25.4 | 0.037 | 686 |
| I-54 | 30 | 0.27 | 111 |
| II-4 | 29.4 | 0.15 | 196 |
| II-7 | 30 | 0.15 | 200 |
| II-9 | 30 | 0.15 | 200 |
| II-24 | 26.2 | 0.078 | 336 |

EXAMPLE 3

Nude Mice Bearing Human Melanoma as a Model System

LOX, a human melanoma cell line, grown subcutaneously in nude mice was excised, trypsinized to yield a single cell suspension using a metal grid with a 4 mm mesh. Red blood cells were lysed by incubation with 0.17 molar ammonium chloride at 4° C. for 20 minutes. Five million viable trypan blue negative cells made up in 0.1 ml of Dulbecco modified Eagles' medium (DME) were injected into the peritoneal cavity of a male athymic Swiss nu/nu mouse. The control group and each treatment group consisted of 5 to 10 mice.

Treatment was commenced the following day by intraperitoneal injection.

Ten control mice received 0.25 ml of 2% dextrose on those days the treated groups were injected with the compounds of this invention. The compounds used in this invention which were tested are listed in Table III below and the results obtained are also shown in Table III. T/C is the ratio, expressed as a percentage of the mean survival age of the treated group to the mean survival age of the untreated control group.

TABLE III

| Compound No. | Dose (mg/kg) | Schedule (i.p. on day) | T/C (%) |
|---|---|---|---|
| I-10 | 15 | 1, 2, 3, 6, 8, 10 | 173 |
| I-46 | 10 | 1, 3, 4, 5, 6, 8 | 175 |
| I-47 | 10 | 1, 3, 5 | 207 |
| I-54 | 6 | 1, 3, 4, 5, 6, 8 | 169 |

EXAMPLE 4

Absorption spectrum of methanol solutions of the compounds used in the present invention was determined. Maximum absorption wavelength and molar absorptivity of respecitive compounds are shown in Tables IV and V.

TABLE IV

| Compound No. | $\lambda_{max}$ (MeOH) [nm] | $\epsilon$ |
|---|---|---|
| I-5 | 460 | $4.45 \times 10^4$ |
| I-6 | 434 | $3.52 \times 10^4$ |
| I-7 | 435 | $3.37 \times 10^4$ |
| I-8 | 467 | $4.50 \times 10^4$ |
| I-9 | 460 | $4.87 \times 10^4$ |
| I-10 | 444 | $3.55 \times 10^4$ |
| I-17 | 462 | $4.17 \times 10^4$ |
| I-18 | 466 | $4.74 \times 10^4$ |
| S-1 (Comparative) | 500 | $7.49 \times 10^4$ |

S-1 compound has the following formula:

TABLE V

| Compound No. | $\lambda_{max}$ (MeOH) [nm] | $\epsilon$ |
|---|---|---|
| II-2 | 520 | $5.78 \times 10^4$ |
| II-3 | 570 | $8.31 \times 10^4$ |
| II-4 | 564 | $7.58 \times 10^4$ |
| II-9 | 582 | $5.80 \times 10^4$ |
| S-2 (Comparative) | 593 | $9.44 \times 10^4$ |

S-2 compound has the following formula:

As is apparent from Tables IV and V, methine compounds used in the present invention have absorption at short wavelength compared with that of comparative and conventional rhodacyanine compounds and therefore methine compounds used in the present invention are preferable as pharmaceutical agents.

While the invention has been described in detail and with reference to specific embodiments thereof, it will be apparent to one skilled in the art that various changes and modifications can be made without departing from the spirit and scope of the invention.

What is claimed is:

1. A pharmaceutical composition comprising:
   (A) a therapeutically effective amount of a methine compound represented by the following Formula (X):

wherein $R_1$ and $R_2$ each represent an alkyl group having 1 to 10 carbon atoms; $R_4$, $R_5$, $R_6$ and $R_7$ together form a benzene ring or a naphthalene ring; or $R_5$ and $R_6$ each represent a hydrogen atom or an alkyl group having 1 to 10 carbon atoms and $R_4$ and $R_7$ together form a single bond;

A represents wherein $R_3$ represents an alkyl group having 1 to 10 carbon atoms;

$R_{10}$, $R_{11}$, $R_{12}$, $R_{13}$, $R_{14}$, and $R_{15}$, which may be the same or different, each represent a hydrogen atom, or $R_{10}$ and $R_{11}$, or $R_{12}$ and $R_{13}$ or $R_{14}$ and $R_{15}$ may be combined to form a benzene ring or a naphthalene ring;

$L_1$ and $L_2$ each represent a methine group or a substituted methine group where said substituent is an alkyl group having 1 to 5 carbon atoms, an aryl group having 6 to 10 carbon atoms, a halogen atom or an alkoxy group having 1 to 5 carbon atoms;

m is 0 or 1,

X represents a pharmaceutically acceptable anion, and k represents a number necessary for adjusting the electric charge of the molecule to zero; and (B) a pharmaceutically acceptable carrier or diluent.

2. The composition according to claim 1 wherein A represents wherein $R_3$, $R_{10}$ and $R_{11}$ are as defined in claim 1.

3. The composition according to claim 1 wherein A represents

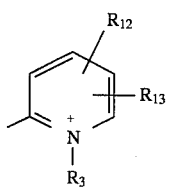

wherein $R_3$, $R_{12}$ and $R_{13}$ are as defined in claim 1.

4. The composition according to claim 1 wherein A represents

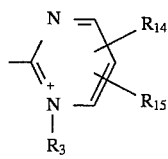

wherein $R_3$, $R_{14}$ and $R_{15}$ are as defined in claim 1.

5. The pharmaceutical composition of claim 1 wherein the methine compound is:

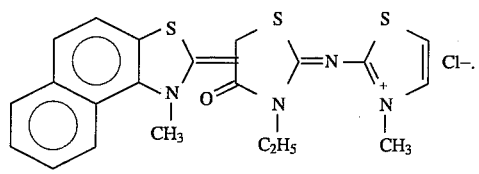

6. A method for treating cancer comprising administering a pharmaceutically effective amount of a methine compound represented by the following formula (X):

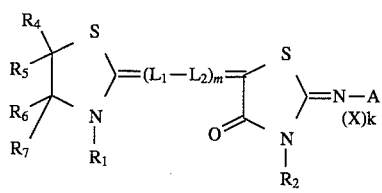

wherein $R_1$ and $R_2$ each represent an alkyl group having 1 to 10 carbon atoms; $R_4$, $R_5$, $R_6$ and $R_7$ together form a benzene ring or a naphthalene ring; or $R_5$ and $R_6$ each represent a hydrogen atom or an alkyl group having 1 to 10 carbon atoms and $R_4$ and $R_7$ together form a single bond;

A represents

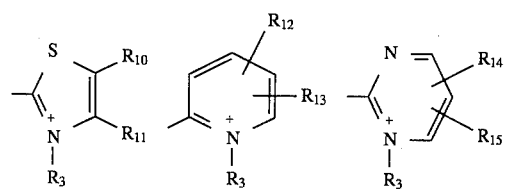

wherein $R_3$ represents an alkyl group having 1 to 10 carbon atoms;

$R_{10}$, $R_{11}$, $R_{12}$, $R_{13}$, $R_{14}$, and $R_{15}$, which may be the same or different, each represent a hydrogen atom, or $R_{10}$ and $R_{11}$, or $R_{12}$ and $R_{13}$ or $R_{14}$ and $R_{15}$ may be combined to form a benzene ring or a naphthalene ring;

$L_1$ and $L_2$ each represent a methine group or a substituted methine group where said substituent is an alkyl group having 1 to 5 carbon atoms, an aryl group having 6 to 10 carbon atoms, a halogen atom or an alkoxy group having 1 to 5 carbon atoms;

m is 0 or 1;

X represents a pharmaceutically acceptable anion, k represents a number necessary for adjusting the electric charge of the molecule to zero;

to a subject afflicted with cancer sensitive to treatment with the compounds of the Formula (X).

7. The method for treating cancer according to claim 6 wherein A is

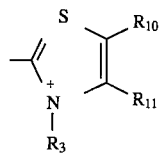

wherein $R_3$, $R_{10}$ and $R_{11}$ are as defined in claim 6.

8. The method for treating cancer according to claim 6 wherein A is

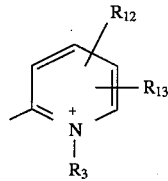

wherein $R_3$, $R_{12}$ and $R_{13}$ are as defined in claim 6.

9. The method for treating cancer according to claim 6 wherein A is

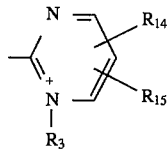

wherein $R_3$, $R_{14}$ and $R_{15}$ are as defined in claim 6.

* * * * *

UNITED STATES PATENT AND TRADEMARK OFFICE
CERTIFICATE OF CORRECTION

PATENT NO. : 5,618,831
DATED : April 8, 1997
INVENTOR(S) : Tadao Shishido; Masayuki Kawakami; Akihiko Ikegawa; Toshinao Ukai; Keizo Koya; Lan Bo Chen.

It is certified that error appears in the above-identified patent and that said Letters Patent is hereby corrected as shown below:

On the title page, item [57] Abstract, and at column 2, lines 35 to 44 delete Formula (I) and insert therefor

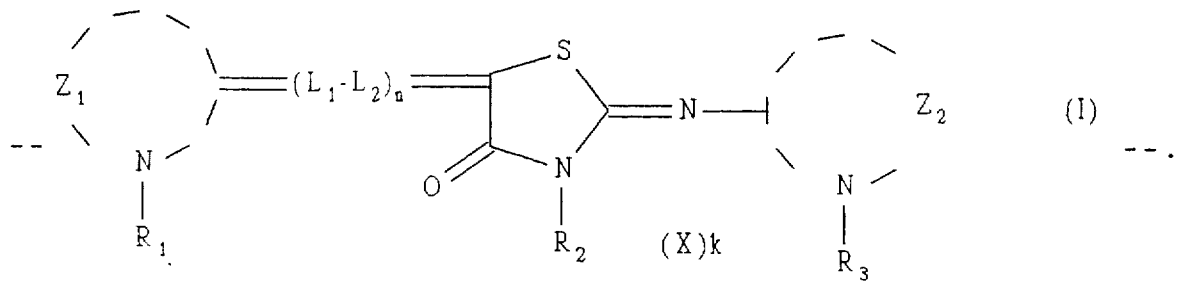

Signed and Sealed this

Twenty-seventh Day of January, 1998

*Attest:*

BRUCE LEHMAN

*Attesting Officer*     *Commissioner of Patents and Trademarks*